US010595771B2

United States Patent
Deirmengian et al.

(10) Patent No.: US 10,595,771 B2
(45) Date of Patent: *Mar. 24, 2020

(54) METHOD OF NORMALIZING IMPLANT STRAIN READINGS TO ASSESS BONE HEALING

(71) Applicant: DePuy Synthes Products, Inc., Raynham, MA (US)

(72) Inventors: Carl Deirmengian, Newtown Square, PA (US); George Mikhail, Chester Springs, PA (US); Glen Pierson, Glenmoore, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 172 days.

This patent is subject to a terminal disclaimer.

(21) Appl. No.: 14/750,716

(22) Filed: Jun. 25, 2015

(65) Prior Publication Data
US 2015/0289796 A1    Oct. 15, 2015

Related U.S. Application Data

(63) Continuation of application No. 12/909,220, filed on Oct. 21, 2010, now Pat. No. 10,441,210.
(Continued)

(51) Int. Cl.
| | |
|---|---|
| A61B 5/00 | (2006.01) |
| A61B 17/80 | (2006.01) |
| A61B 5/07 | (2006.01) |
| A61B 5/103 | (2006.01) |
| A61F 2/46 | (2006.01) |

(Continued)

(52) U.S. Cl.
CPC ............ *A61B 5/4504* (2013.01); *A61B 5/076* (2013.01); *A61B 5/103* (2013.01); *A61B 5/686* (2013.01); *A61B 17/80* (2013.01); *A61F 2/4657* (2013.01); *A61B 2017/00221* (2013.01); *A61B 2090/064* (2016.02); *A61B 2562/028* (2013.01);
(Continued)

(58) Field of Classification Search
CPC . A61B 5/4504; A61B 17/80; A61B 2019/464; A61B 2562/0261; A61F 2/4657; A61F 2002/4666
See application file for complete search history.

(56) References Cited

U.S. PATENT DOCUMENTS

| | | | |
|---|---|---|---|
| 6,001,099 A | 12/1999 | Huebner | |
| 6,034,296 A | 3/2000 | Elvin et al. | |

(Continued)

FOREIGN PATENT DOCUMENTS

| | | |
|---|---|---|
| DE | 198 10 182 | 3/2000 |
| DE | 102006006341 | 8/2007 |

(Continued)

*Primary Examiner* — Devin B Henson
(74) *Attorney, Agent, or Firm* — Fay Kaplun & Marcin, LLC

(57) ABSTRACT

A device for treating bone in a living body includes (a) comprises an implant configured for attachment to a bone; (b) a first sensor measuring a strain on a first portion of the implant, the first portion of the implant being configured to be mechanically coupled to a weakened portion of a bone when the implant is coupled to the bone in a target position in combination; and (c) a second sensor measuring strain in a non-weakened portion of the bone.

20 Claims, 4 Drawing Sheets

Related U.S. Application Data

(60) Provisional application No. 61/253,583, filed on Oct. 21, 2009.

(51) Int. Cl.
*A61B 90/00* (2016.01)
*A61B 17/00* (2006.01)

(52) U.S. Cl.
CPC . *A61B 2562/0261* (2013.01); *A61B 2562/166* (2013.01); *A61F 2002/4666* (2013.01)

(56) References Cited

U.S. PATENT DOCUMENTS

| | | | |
|---|---|---|---|
| 6,273,863 | B1 | 8/2001 | Avni et al. |
| 6,610,096 | B2 | 8/2003 | MacDonald |
| 8,083,741 | B2 | 12/2011 | Morgan et al. |
| 2003/0040806 | A1 | 2/2003 | MacDonald |
| 2005/0010300 | A1 | 1/2005 | Disilvestro et al. |
| 2005/0085814 | A1 | 4/2005 | Sherman et al. |
| 2006/0052782 | A1* | 3/2006 | Morgan ................. A61N 1/205 606/60 |
| 2008/0147125 | A1 | 6/2008 | Colleran et al. |
| 2008/0300597 | A1* | 12/2008 | Morgan ............... A61B 5/0031 606/62 |

FOREIGN PATENT DOCUMENTS

| | | |
|---|---|---|
| DE | 102006034041 | 1/2008 |
| DE | 102010022434 | 12/2011 |
| JP | 2005-532123 | 10/2005 |
| JP | 2006-506194 | 2/2006 |
| JP | 2007-530083 | 11/2007 |
| JP | 2008-501488 | 1/2008 |
| JP | 2009-505751 | 2/2009 |
| WO | 2004/005872 | 1/2004 |
| WO | 2004-045455 | 6/2004 |
| WO | 2005/120203 | 12/2005 |
| WO | 2007/025191 | 3/2007 |
| WO | 2011/050149 | 4/2011 |

* cited by examiner

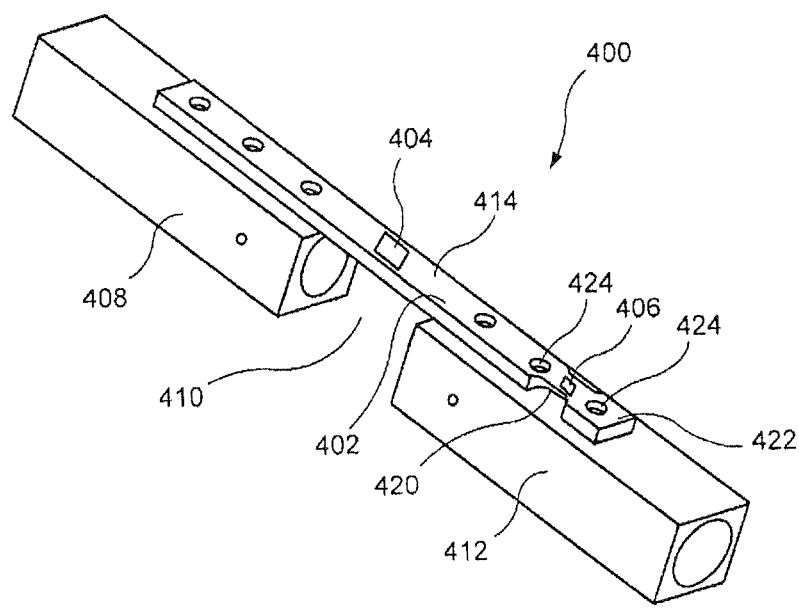
F I G. 5

METHOD OF NORMALIZING IMPLANT STRAIN READINGS TO ASSESS BONE HEALING

PRIORITY CLAIM

The present application is a Continuation Application of U.S. patent application Ser. No. 12/909,220 filed on Oct. 21, 2010; which claims the priority to the U.S. Provisional Application Ser. No. 61/253,583 filed on Oct. 21, 2009. The entire disclosures of these patents/applications are expressly incorporated herein by reference.

FIELD OF THE INVENTION

The present invention relates to a system and method for tracking the progress of bone healing and, in particular, systems and methods that calculate a ratio of strain at multiple locations along an implant and/or a bone

BACKGROUND

Strain gages can be placed on orthopedic implants to track the progress of bone Healing. Upon initial implantation, the implants are expected to experience higher levels of strain which decrease during healing as the bone begins to share more of the load with the implant. Currently, however, implant strain values need to be assessed with a known load applied to the bone in order to evaluate bone healing.

SUMMARY OF THE INVENTION

The present invention is directed to a device for treating bone in a living body, comprising an implant configured for attachment to a bone and a first sensor measuring a strain on a first portion of the implant, the first portion of the implant being configured to be mechanically coupled to a weakened portion of a bone when the implant is coupled to the bone in a target position in combination with a second sensor measuring strain in a non-weakened portion of the bone.

BRIEF DESCRIPTION OF THE DRAWINGS

FIG. 5 shows a perspective view of a system according to a fourth exemplary embodiment of the present invention.

DETAILED DESCRIPTION

Figure 1:
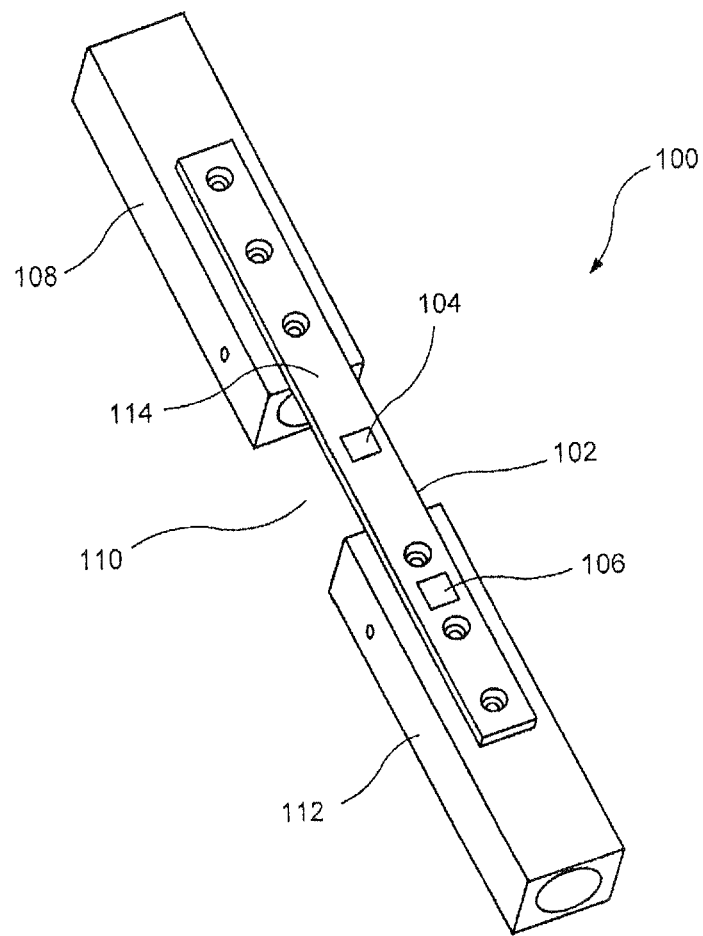
FIG. 1 shows a perspective view of a system according to a first exemplary embodiment of the present invention.

The present invention may be further understood with reference to the following description and the appended drawings, wherein like elements are referred to with the same reference numerals. The exemplary embodiment of the present invention relate to a system and method for tracking the progress of bone healing. In particular, the exemplary embodiments describe systems and methods that calculate a ratio of strain at multiple locations along an implant and/or a bone. An exemplary embodiment of the system may include a first sensor on a surface of the implant adapted to be positioned at a location proximate a weakened portion of the bone. Strain on the implant at this location will be affected by the strength or stiffness of the weakened bone and the load placed on the bone by the patient. A second sensor may be placed on the implant at a location in which strain measured by the second sensor is affected only by the load placed on the bone such that the measured strain is substantially unchanged by the bone healing process. Thus, a ratio between the strains measured by the first and second sensors provides information corresponding to bone healing, regardless of the load on the bone. It will be understood by those of skill in the art that although the exemplary embodiment specifically describe tracking the healing progress of a leg bone, the present invention may be used to track the progress of healing of any load bearing bone. It will also be understood by those of skill in the art that although the exemplary embodiments specifically show and describe two sensors, the present invention may include additional sensors along different areas of the bone to determine ratios corresponding to the bone healing progress of the different areas. In addition, although exemplary embodiments show a bone plate, the present invention may be used with any other fixation element such as, for example, screws, intramedullary devices, external fixators, spine fixation implants and prosthetics.

As shown in FIG. 1, a system 100 according to a first exemplary embodiment of the invention comprises an implant 102 (e.g., a bone plate) and first and second sensors 104, 106, respectively. The implant 102 is configured for fixation over a target portion of a bone 108 to, for example, fix a fracture 110 or to support a weakened portion of the bone 108. The first and second sensors 104, 106 are mounted along a surface 114 of the implant 102 such that the first and second sensors 104, 106 may be mechanically coupled to the bone 108. Although the surface 114 is shown as facing away from the bone 108 when the implant 102 is fixed to the bone 108 in a desired location, it will be understood by those of skill in the art that the sensors 104, 106 may be mounted along any surface of the implant 102. For example, the sensors 104, 106 may also be mounted on a surface of the implant 102 facing the bone 108 or a surface on a side of the implant 102. The first and second sensors 104, 106, respectively, are positioned on the implant 102 so that, when the implant is in a desired position on the bone 108, the first sensor 104 is located over a site of the fracture 110 while the second sensor 106 is separated from the fracture 110 over a healthy (i.e., solid) portion 112 of the bone 108 to measure levels of strain and/or load on the implant 102, at these positions along the implant 102. The second sensor 106 should be isolated between two screws locked in a healthy portion 112 of the bone 108 to measure a load on the bone 108.

The sensors 104, 106 in this embodiment may be passively powered MEMs sensors that are used to measure strain and include an interface for wireless connection to a data collection device as would be understood by those skilled in the art. In another embodiment, the sensors 104, 106 may be powered chips that are connected to a printed circuit board (PCB). This permits strain on the implant 102 to be measured and transmitted to the data collection device for further processing without physically accessing the sensors 104, 106. It will be understood by those of skill in the art that the strain measurements detected by the sensors 104, 106 are not required to represent actual strain values, but may include any signal that changes based on changing strains of their substrates. For example, the MEMS sensors 104, 106 may be RF devices that deform when a strain is placed thereon, resulting in a frequency shift caused by a change in capacitance of the sensors 104, 106 such that the frequency shift corresponds to a change in strain. As would be understood by those skilled in the art, an external device may be employed to wirelessly provide a signal to the sensors 104, 106. Changes in a returned signal may then be measured to determine a level of strain to which the sensor is subject. A ratio of the strain measured by the first sensor 104 to the strain measured by the second sensor 106 may then be determined by a physician or other professional to track healing progress. Alternatively, the ratio may be determined by a processing device that may also store the strain measurements and the determined ratios (e.g., in an internal memory or on an external storage device) so that changes in the ratio may be reviewed to more fully understand the progression of the healing over time.

It will be understood by those of skill in the art that when the bone 108 is initially broken or fractured, strain on the implant 102 at the location of the fracture 110 will vary based on changing mechanical properties of the bone 108 during the healing process and the load placed on the bone 108 (e.g., the weight that the patient places on the leg) while the strain measured in the healthy portion 112 varies based only on the load placed on the bone 108. Thus, taking a ratio of the strains measured by the two sensors 104, 106 normalizes the effects of the load on the sensors 104, 106 providing data corresponding to the stiffness of the bone 108 at the fracture site 110. The ratio of the measurements from the first sensor 104 to the measurements from the second sensor 106 during the healing process should trend in a decreasing pattern over time, whereas a lack of healing would show no recognizable trend over time.

Figure 2:
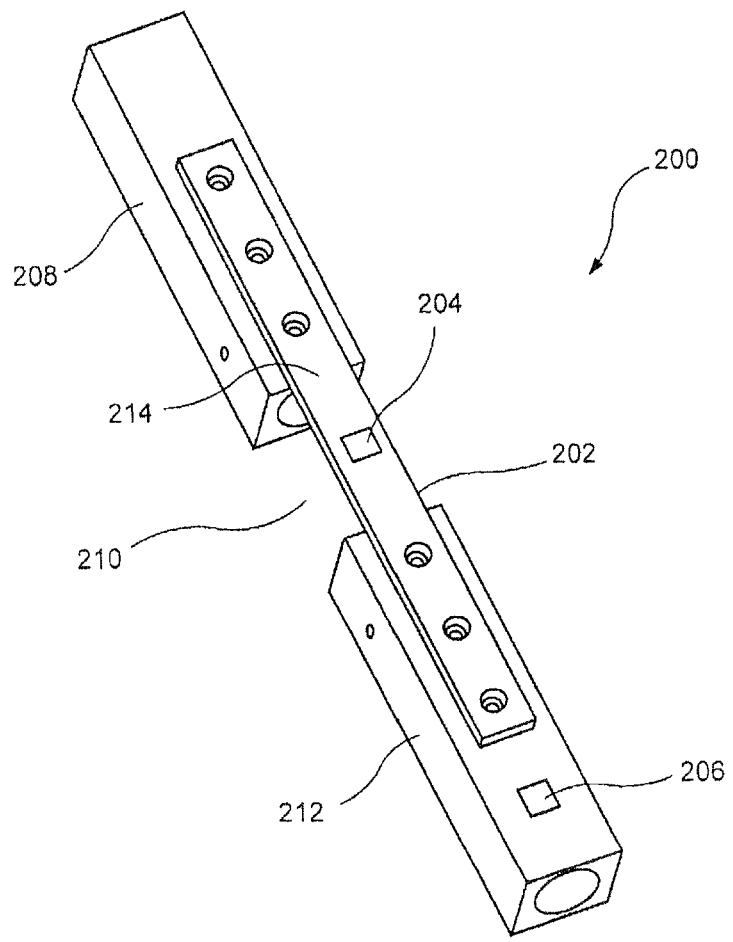
FIG. 2 shows a perspective view of a system according to a second exemplary embodiment of the present invention.

As shown in FIG. 2, a system 200 according to a second exemplary embodiment of the invention is substantially similar to the system 100, including an implant 202 and at least two sensors 204, 206. However, rather than both sensors 204, 206 being positioned on the implant 202, the first sensor 204 is located on a surface 214 of the implant 202 in a position corresponding to a fracture of a bone 208, while the second sensor 206 is placed directly on a solid portion 212 of the bone 208, outside a perimeter of the implant 202. Thus, the first sensor 204 measures strain on the implant 202 at a position corresponding to the site of the fracture 210 while the second sensor 206 measures strain on the solid portion 212 of the bone 208. Similarly to the system 100, a ratio between the strains measured by the first and second sensors 204, 206 is determined and tracked to study the progress of healing in the bone 208. As indicated above, the ratio of the strain measurements from the first sensor 204 to the strain measurements from the second sensor 206 trend in a decreasing pattern as the bone 208 heals, whereas a lack of healing will show no recognizable trend over time.

Figure 4:
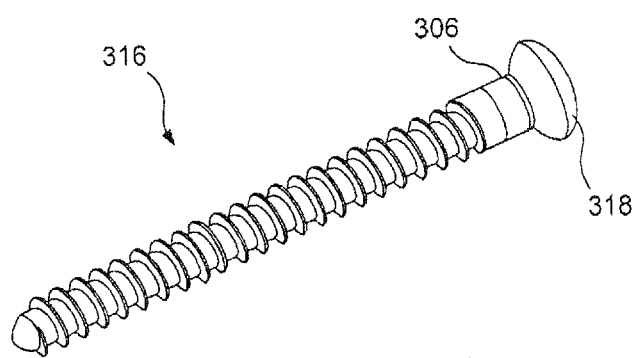
FIG. 4 shows a side view of a bone fixation element of the system of FIG. 3.
Figure 3:
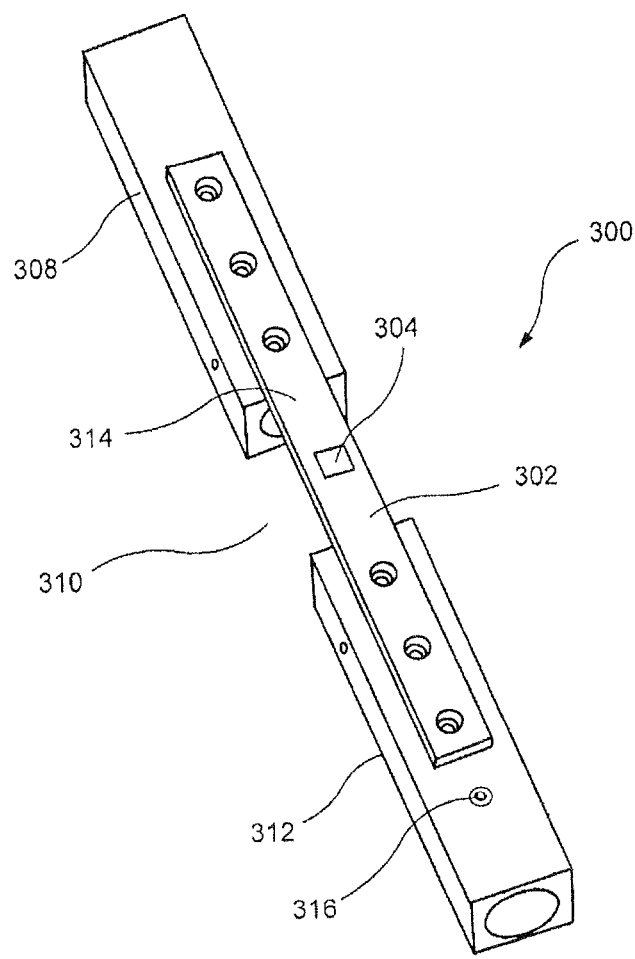
FIG. 3 shows a perspective view of a system according to a third exemplary embodiment of the present invention.

As shown in FIGS. 3-4, a system 300 according to a third exemplary embodiment of the invention is substantially similar to the system 200, comprising an implant 302 and at least two sensors 304, 306. Similarly to the first sensor 204, the first sensor 304 is placed on a surface 314 of the implant 302 in a location corresponding to a position of a fracture 310 of a bone 308 (when the implant 302 is mounted on the bone 308 in a desired position) to measure strain on the implant 302 at the position of the fracture 310 while the second sensor 306 is placed directly on a solid portion 312 of the bone 308. However, rather than being placed on an exterior surface of the bone 308, the second sensor 306 is placed within the solid portion 312 via, for example, a bone fixation element 316 (e.g., screw).

The second sensor 306 may be attached adjacent to a proximal end 318 of the bone fixation element 316 such that when the bone fixation element 316 is inserted into the solid portion 312 of the bone, the second sensor 306 contacts a cortical wall of the bone 308. The second sensor 306 may be printed or mounted around a portion of the bone fixation element 316 to measure deformation of the bone 308 which is directly related to strain on the bone 308. The ratio of the measurements from the first sensor 304 to those of the second sensor 306 may then be determined to track healing progress in the same manner described above.

As shown in FIG. 5, a system 400 according to a fourth exemplary embodiment of the invention is substantially similar to the system 100, comprising an implant 402 and first and second sensors 404, 406, respectively, both of which are mounted on the implant 402. Similarly to the first sensor 104, the first sensor 404 is located on the implant 402 in a position which, when the implant 402 is in the desired position, corresponds to the location of a fracture 410 so that the first sensor 404 measures strain on the implant 402 at a position corresponding to the site of the fracture 410. The second sensor 406 is positioned on a portion 420 of the implant 402 having greater flexibility than the portion of the implant 402 on which the first sensor 404 is mounted. For example, the portion 420 may be made more flexible than other portions of the implant 402 by reducing a width (i.e., an extent of the implant 402 across a bone facing surface thereof in a direction perpendicular to a longitudinal axis of the implant 402) and/or a thickness of the portion 420 (i.e., a distance between the bone facing surface and a surface thereof which faces away from the bone) as compared to remaining portions of the implant 402. In a preferred embodiment, the flexible portion 420 is adjacent to an end 422 of the implant 402 so that the second sensor 406 is separated from the fracture 410 by a distance great enough to ensure that the underlying portion 412 of the bone 408 is solid.

The second sensor 406 on the flexible portion 420 of the implant 402 is fixed to the solid portion 412 of the bone 408 via, for example, locking screws inserted in holes 424 on opposing sides thereof. The second sensor 406 measures strain on a portion of the implant 402 corresponding to the solid portion 412 of the bone 408 so that measurements from the second sensor 406 may be used to normalize measurements from the first sensor. Similarly to the placement of a sensor directly in or on a bone, as described in conjunction with systems 200 and 300, placing the second sensor 406 on a more flexible portion 420 of the implant 402 between two locked screws permits a more accurate measurement of the strain on the underlying solid portion 412 of the bone 408, as compared to the results from placing the second sensor 406 on a stiffer portion of the implant 402. The ratio of the measurements from the first sensor 404 to the measurements from the second sensor 406 during the healing process should trend in a pattern indicating an increasing stiffness of the bone 408 over time, whereas a lack of healing should show no recognizable trend over time.

It will be understood by those of skill in the art that other mechanisms may be employed for normalizing measurements of strain on a portion of an implant which, when mounted on a bone in a target location, corresponds to a position of a fracture or other weakened portion of that bone. For example, the patient may be provided with load sensors on which to push or stand with the affected limb such that a load measurement may be taken simultaneously with a strain measurement of the sensor on the implant. Alternatively, the patient may be provided with a sensor (e.g., placed in the sole of a shoe) to measure the load placed on the affected leg, if the affected bone is the femur or tibia.

It will be apparent to those skilled in the art that various modifications and variations can be made in the structure and the methodology of the present invention, without departing from the spirit or the scope of the invention. Thus, it is intended that the present invention cover the modifications and variations of this invention provided that they come within the scope of the appended claims and their equivalents.

What is claimed is:

1. A system for treating a bone, comprising:
an implant sized and shaped to be attached to a bone and including a first sensor and a second sensor, the first sensor positioned on a first portion of the implant which extends over a weakened portion of bone in an operative position, the first sensor being configured to measure a first strain on the first portion, the second sensor being positioned on a second portion of the implant which extends over an unweakened portion of bone in the operative position, the second sensor being configured to measure a second strain on the second portion; and
a processing device calculating a ratio of the first strain to the second strain to normalize an effect of loads on the bone and track healing of the bone.

2. The system of claim 1, wherein the second sensor is isolated between two fixation element receiving holes of the implant.

3. The system of claim 1, wherein the implant is a plate configured to be coupled to a bone overlying a fracture site, the fracture site comprising the weakened portion of bone.

4. The system of claim 1, wherein the implant includes a rigid portion having a first bending stiffness and a less rigid portion having a second bending stiffness less than the first bending stiffness of the rigid portion.

5. The system of claim 4, wherein the second portion of the implant comprises the less rigid portion of the implant.

6. The system of claim 1, wherein one of the first and second sensors is a strain sensor measuring a strain on a bone to which the implant is mounted.

7. The system of claim 1, wherein the first and second sensors are one of MEMs sensors and power chips connected to a printed circuit board.

8. The system of claim 1, wherein the processing device includes an external data gathering unit which wirelessly receives measured first and second strains.

9. The system of claim 2, further comprising:
first and second locking screws which, when the implant is coupled to the bone in an operative position, are inserted through the two bone fixation element receiving holes on opposing sides of the second sensor.

10. A system for treating a bone, comprising:
an implant configured for attachment to a bone, the implant including a first sensor on a first portion of the implant which, in an operative position, is configured to extend over a weakened portion of the bone to measure a first strain on the first portion;
a second sensor positioned over an unweakened portion of bone to measure a second strain on the second portion; and
a processing device calculating a ratio of the first strain to the second strain to normalize an effect of loads on the bone.

11. The system of claim 10, wherein the second sensor is positioned on a second portion of the implant which, in the operative position, extends over the unweakened portion of bone.

12. The system of claim 10, wherein the second sensor is mounted to a bone fixation element which, in an operative position, is inserted into the unweakened portion of bone, the second sensor being positioned on the bone fixation element so that the second sensor contacts a cortical wall when the bone fixation element is inserted into the bone.

13. The system of claim 12, wherein the second sensor extends about a circumference of a proximal portion of the bone fixation element.

14. The system of claim 10, wherein the implant is a plate configured to be coupled to a bone overlying a fracture site.

15. The system of claim 10, wherein the first and second sensors are one of MEMs sensors and powered chips connected to a printed circuit board.

16. A method for treating a bone, comprising:
positioning an implant in an operative position over a selected portion of a bone so that a first portion of the implant extends over a weakened portion of the bone and a second portion of the implant extends over an unweakened portion of the bone;
measuring a first strain via a first sensor on the first portion of the implant;
positioning a second sensor over the unweakened portion of the bone;
measuring a second strain via the second sensor; and
calculating a ratio of the first strain to the second strain to normalize an effect of loads on the bone and track healing of the bone.

17. The method of claim 16, wherein, in the operative position, the second sensor is located over the unweakened portion of bone.

18. The method of claim 16, wherein the second sensor is mounted to a portion of a bone fixation element, further comprising the step of inserting the bone fixation element through the implant into the unweakened portion of bone so that the second sensor contacts a cortical wall of the bone.

19. The method of claim 16, further comprising:
wirelessly transmitting the first and second strains to an external data gathering unit.

20. The method of claim 16, wherein the first and second sensors are one of MEMs sensors and powered chips connected to a printed circuit board.

* * * * *